US010881738B2

(12) United States Patent
Riggs-Sauthier et al.

(10) Patent No.: US 10,881,738 B2
(45) Date of Patent: *Jan. 5, 2021

(54) OLIGOMER-BETA BLOCKER CONJUGATES

(71) Applicant: Nektar Therapeutics, San Francisco, CA (US)

(72) Inventors: Jennifer Riggs-Sauthier, Huntsville, AL (US); Franco J. Duarte, Walnut Creek, CA (US); Aaron S. Hammons, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/277,785

(22) Filed: Feb. 15, 2019

(65) Prior Publication Data
US 2019/0175743 A1     Jun. 13, 2019

Related U.S. Application Data

(63) Continuation of application No. 15/690,106, filed on Aug. 29, 2017, now Pat. No. 10,251,959, which is a continuation of application No. 12/530,412, filed as application No. PCT/US2008/003352 on Mar. 12, 2008, now Pat. No. 9,782,488.

(60) Provisional application No. 60/906,417, filed on Mar. 12, 2007.

(51) Int. Cl.
*A61K 31/135* (2006.01)
*C07C 211/00* (2006.01)
*A61K 47/60* (2017.01)

(52) U.S. Cl.
CPC ................... *A61K 47/60* (2017.08)

(58) Field of Classification Search
CPC .................................................. A61K 47/60
See application file for complete search history.

(56) References Cited

U.S. PATENT DOCUMENTS

| | | |
|---|---|---|
| 3,337,628 A | 8/1967 | Crowther et al. |
| 3,520,919 A | 7/1970 | Crowther et al. |
| 3,551,493 A | 12/1970 | Ruschig et al. |
| 3,649,691 A | 3/1972 | Shavel, Jr. et al. |
| 3,655,663 A | 4/1972 | Wasson et al. |
| 3,657,237 A | 4/1972 | Weinstock et al. |
| 3,663,607 A | 5/1972 | Barrett et al. |
| 3,836,671 A | 9/1974 | Barrett et al. |
| 3,857,952 A | 12/1974 | Wooldridge et al. |
| 3,873,600 A | 3/1975 | Brandstrom et al. |
| 3,910,924 A | 10/1975 | Tamura et al. |
| 3,935,267 A | 1/1976 | Hauck et al. |
| 3,998,835 A | 12/1976 | Troxler et al. |
| 4,012,444 A | 3/1977 | Lunts et al. |
| 4,252,984 A | 2/1981 | Manoury et al. |
| 4,258,062 A | 3/1981 | Jonas et al. |
| 4,463,176 A | 7/1984 | Dennis et al. |
| 4,593,119 A | 6/1986 | Erhardt et al. |
| 4,795,715 A | 1/1989 | Eller et al. |
| 5,672,662 A | 9/1997 | Harris et al. |
| 5,783,178 A | 7/1998 | Kabanov et al. |
| 9,782,488 B2 | 10/2017 | Riggs-Sauthier et al. |
| 2005/0032879 A1 | 2/2005 | Okarter et al. |
| 2005/0136031 A1 | 6/2005 | Bentley et al. |
| 2008/0021005 A1 | 1/2008 | Cheu et al. |
| 2010/0227865 A1 | 9/2010 | Riggs-Sauthier et al. |
| 2017/1360948 | 12/2017 | Riggs-Sauthier et al. |

FOREIGN PATENT DOCUMENTS

| | | |
|---|---|---|
| CH | 469 002 | 2/1969 |
| CH | 472 404 | 3/1969 |
| FR | 6379 | 4/1967 |
| GB | 1148563 | 4/1969 |
| WO | WO 02/098949 | 12/1999 |
| WO | WO 99/64050 | 12/1999 |
| WO | WO 00/67801 | 11/2000 |
| WO | WO 03/084926 | 10/2003 |
| WO | WO 2005/053685 | 6/2005 |
| WO | WO 2005/058367 | 6/2005 |

OTHER PUBLICATIONS

Anderson et al., "Reduction of First-Pass Metabolism of Propranolol after Oral Administration of Ester Prodrugs", International Journal of Pharmaceutics, vol. 43, pp. 261-265, (1988).

Chen et al., "Synthesis and Properties of ABA Amphiphiles", J. Org. Chem., vol. 64, pp. 6870-6873, (1999).

Cynkowska et al. "Novel Antiglaucoma Prodrugs and Codrugs of Ethacrynic Acid", Bioorganic & Medicinal Chemistry Letters, vol. 15, pp. 3524-3527, (2005).

Ertl et al., "Fast Calculation of Molecular Polar Surface Area as a Sum of Fragment-Based Contributions and Its Application to the Prediction of Drug Transport Properties", J. Med. Chem., vol. 43, pp. 3714-3717, (2000).

Frang et al., "Nonradioactive GTP Binding Assay to Monitor Activation of G Protein-Coupled Receptors", Assay and Drug Dev. Tech., vol. 1, No. 2, pp. 275-280, (2003).

Hovgaard et al. "Drug Delivery Studies in Caco-2 Monolayers. Synthesis, Hydrolysis, and Transport of O-Cyclopropane Carboxylic Acid Ester Prodrugs of Various β-Blocking Agents", Pharmaceutical Research, vol. 12, No. 3, pp. 387-392, (1995).

Iwamoto et al., "Avoidance of First-Pass Metabolism of Propranolol after Rectal Administration as a Function of the Absorption Site", Pharmaceutical Research, pp. 53-54, (1985).

Jordan, "How an Increase in the Carbon Chain Length of the Ester Moiety Affects the Stability of a Homologous Series of Oxprenolol Esters in the Presence of Biological Enzymes", Journal of Pharmaceutical Sciences, vol. 87, No. 7, pp. 880-885, (1998).

(Continued)

*Primary Examiner* — Shobha Kantamneni
(74) *Attorney, Agent, or Firm* — Jacqueline F. Mahoney

(57) ABSTRACT

The invention provides small molecule drugs that are chemically modified by covalent attachment of a water-soluble oligomer. A conjugate of the invention, when administered by any of a number of administration routes, exhibits a different biological membrane crossing rate as compared to the biological membrane crossing rate of the small molecule drug not attached to the water-soluble oligomer.

10 Claims, No Drawings

(56) References Cited

OTHER PUBLICATIONS

Kelder et al., "Polar Molecular Surface as a Dominating Determinant for Oral Absorption and Brain Penetration of Drugs", Pharm. Res., vol. 16, No. 10, pp. 1514-1519, (1999).
Klinker et al., "G-Protein-coupled Receptors in HL-60 Human Leukemia Cells", Gen. Pharmac., vol. 27, No. 1, pp. 33-54, (1996).
Minneman et al., "Simultaneous Determination of Beta-1 and Beta-2-Adrenergic Receptors in Tissues Containing Both Receptor Subtypes", Molec. Pharm., vol. 16, pp. 34-46, (1979).
Pech et al., "Tensioactivity and Supramolecular Organization of the Palmitoyl Prodrug of Timolol", Pharmaceutical Research, vol. 14, No. 1, pp. 37-41, (1997).
Quan et al., "Controllable selective enzymatic synthesis of N-acyl and O-acylpropranolol vinyl esters and preparation of polymeric prodrug of propranolol", Journal of Molecular Catalysis B: Enzymatic, vol. 44, pp. 1-7, (2007).
Ranucci et al., "On the suitability of urethane bonds between the carrier and the drug moiety in poly(ethylene glycol)-based oligomeric prodrugs", J. Biomat. Sci., vol. 6, No. 2, pp. 133-139, (1994).
Seifert et al., "Incomplete functional differentiation of HL-60 leukemic cells by synthetic lipopeptides", Eur. J. Biochem., vol. 203, pp. 143-151, (1992).
Shameem et al., "An In-vitro and In-vivo Correlative Approach to the Evaluation of Ester Prodrugs to Improve Oral Delivery of Propranolol", J. Pharm. Pharmacol., vol. 45, pp. 246-252, (1993).
Takahashi et al., "Highly Efficient Asymmetric Hydrogenation of Amino Ketone Derivatives Leading to Practical Syntheses of (S)—Propranolol and Related Compounds", J. Am. Chem. Soc., vol. 112, pp. 5876-5878, (1990).
Uloth et al., "Sulfonanilides. I. Monoalkyl-and Arylsulfonamidophenethanolamines", J. Med. Chem., vol. 9, pp. 88-97, (1966).
PCT International Search Report corresponding to PCT Application No. PCT/US2008/003352 dated Jul. 23, 2008.
PCT International Preliminary Report on Patentability corresponding to PCT Application No. PCT/US2008/003352 dated Sep. 24, 2009.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-$1^{st}$, (Jan. 2003).
NOF Corporation, PEG Derivatives, Phospholipid and Drug Delivery Materials for Pharmaceuticals, 27 pages, Catalogue 2003-$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
POLYPURE Products, PEG amines; PEG acids and amino acids; PEG thiols and disulfides; Biotins, 5 pages, (Apr. 2004).
POLYPURE Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).

OLIGOMER-BETA BLOCKER CONJUGATES

CROSS REFERENCE TO RELATED APPLICATION

This application is a continuation of U.S. patent application Ser. No. 15/690,106, filed Aug. 29, 2017, now U.S. Pat. No. 10,251,959, which is a continuation of U.S. patent application Ser. No. 12/530,412, filed Mar. 17, 2010, now U.S. Pat. No. 9,782,488, which is a 35 U.S.C § 371 application of International Application No. PCT/US2008/003352, filed Mar. 12, 2008, designating the United States, which claims the benefit of priority under 35 U.S.C. § 119(e) to U.S. Provisional Application No. 60/906,417, filed Mar. 12, 2007, all of which are incorporated herein by reference in their entireties.

FIELD OF THE INVENTION

This invention comprises (among other things) chemically modified beta blockers that possess certain advantages over beta blockers lacking the chemical modification. The chemically modified beta blockers described herein relate to and/or have application(s) in (among others) the fields of drug discovery, pharmacotherapy, physiology, organic chemistry and polymer chemistry.

BACKGROUND OF THE INVENTION

Beta-adrenergic receptor antagonists ("beta blockers") represent a broad class of agents employed in the treatment of individuals suffering from a variety of disorders. In the treatment of an individual suffering from hypertension, for example, administration of a beta blocker may lower blood pressure. In addition, individuals suffering from cardiac arrhythmias often benefit from the administration of a beta blocker. Other applications in which beta blockers have been used include the treatment of individuals suffering from migraine, congestive heart failure, angina, anxiety and depression. As a class, beta blockers represent an important and widely used tool in pharmacotherapy.

Although beta blockers serve an important role in treating patients, their use is sometimes associated with (among other things) extensive metabolism in the liver as well as certain CNS side effects. Although some beta blockers (such as pindolol, sotalol and carteolol) have no significant first-pass effect, the reduction of CNS side effects from even these beta blockers would enhance their desirability as therapeutic drugs.

One approach for avoiding the problems associated with extensive first pass metabolism is to administer the drug via intravenous administration. Indeed, when propranolol is administered by the intravenous route, much smaller doses are required to achieve a therapeutic effect than when it is given orally. Intravenous administration, however, requires the use of trained clinical personnel, which may be inconvenient or impractical. In such a case, an orally administrable dosage form of a beta blocker not prone to extensive first pass metabolism would be preferred.

Many beta blockers exert CNS effects as these molecules often penetrate the blood-brain barrier. For example, administration of beta blockers has been associated with dizziness, peripheral neuropathy, paresthesias, sleep disturbances and seizures. As a consequence, pharmacotherapy with beta blockers would be improved if these and/or other side effects associated with their use could be decreased.

The present invention seeks to address these and other needs in the art.

SUMMARY OF THE INVENTION

In one or more embodiments of the invention, a compound is provided, the compound comprising a beta blocker residue covalently attached via a stable or degradable linkage to a water-soluble, non-peptidic oligomer.

Exemplary compounds of the invention include those having the following structure:

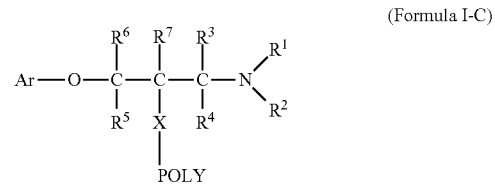

(Formula I-C)

wherein:

$R^1$ selected from the group consisting of is hydrogen, lower alkyl, lower alkenyl, hydroxy-lower alkenyl, and phenyl-lower alkyl, $R^2$ is selected from the group consisting of hydrogen, alkyl (preferably lower alkyl, such as isopropyl or tertiary butyl), hydroxyalkyl (preferably hydroxy-lower alkenyl), $C_{3-6}$ cycloalkyl, phenyl alkyl (preferably phenyl-lower alkyl), aralkyl (optionally mono- to tri-substituted by alkyl, alkoxy, OH, F, and/or Cl or monosubstituted with methylenedioxy), alkenyl (preferably lower alkenyl), hydroxyalkenyl (preferably hydroxy-lower alkenyl), cyano, branched cyano, phenyl (optionally substituted with alkyl), halophenyl (optionally substituted with alkyl), alkoxy, alkoxyphenyl, acyl, acylamino, aralkyl, aralkyl wherein the aryl radical is mono- to tri-substituted by alkyl, alkoxy, OH, F, and/or Cl or mono substituted by methylenedioxy, or $R^1$ and $R^3$ can be joined together with the N to form heterocyclic structure;

$R^3$ is H or lower alkyl;
$R^4$ is H or lower alkyl;
$R^5$ is H or lower alkyl;
$R^6$ is H or lower alkyl;
$R^7$ is H or lower alkyl;
Ar is an aromatic-containing moiety;
X is a spacer moiety; and
POLY is a water-soluble, non-peptidic oligomer.

Further exemplary compounds of the invention include those having the following structure:

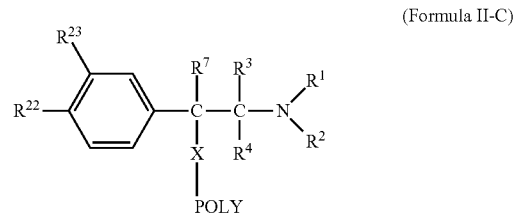

(Formula II-C)

wherein:
$R^1$ is H or lower alkyl;
R" is selected from the group consisting of an arylalkyl group and an aryloxyalkyl group;

$R^3$ is H or lower alkyl;
$R^4$ is H or lower alkyl;
$R^7$ is H or lower alkyl;
$R^{22}$ is —OH or —NH—SO$_2$—CH$_3$;
$R^{23}$ is H or —C(O)—NH$_2$;
X is a spacer moiety; and
POLY is a water-soluble, non-peptidic oligomer.

The "beta blocker residue" is a compound having a structure of a beta blocker that is altered by the presence of one or more bonds, which bonds serve to attach (either directly or indirectly) one or more water-soluble, non-peptidic oligomers. In this regard, any compound having beta-blocker activity can be used. Exemplary beta blockers have a structure encompassed by at least one of the structures defined herein as Formula I and Formula II. With respect to beta blockers having a structure encompassed by Formula I, structures of Formula I are defined as follows:

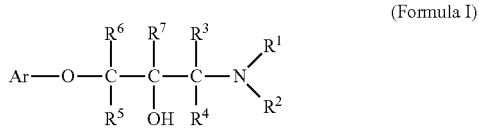

(Formula I)

wherein:

$R^1$ is selected from the group consisting of hydrogen, lower alkyl, lower alkenyl, hydroxy-lower alkenyl, and phenyl-lower alkyl, $R^2$ is selected from the group consisting of hydrogen, alkyl (preferably lower alkyl, such as isopropyl or tertiary butyl), hydroxyalkyl (preferably hydroxy-lower alkenyl), C$_{3-6}$ cycloalkyl, phenyl alkyl (preferably phenyl-lower alkyl), aralkyl (optionally mono- to tri-substituted by alkyl, alkoxy, OH, F, and/or Cl or monosubstituted with methylenedioxy), alkenyl (preferably lower alkenyl), hydroxyalkenyl (preferably hydroxy-lower alkenyl), cyano, branched cyano, phenyl (optionally substituted with alkyl), halophenyl (optionally substituted with alkyl), alkoxy, alkoxyphenyl, acyl, acylamino, aralkyl, aralkyl wherein the aryl radical is mono- to tri-substituted by alkyl, alkoxy, OH, F, and/or Cl or mono substituted by methylenedioxy, or $R^1$ and $R^2$ can be joined together with the N to form heterocyclic structure;

$R^3$ is H or lower alkyl;
$R^4$ is H or lower alkyl;
$R^5$ is H or lower alkyl;
$R^6$ is H or lower alkyl;
$R^7$ is H or lower alkyl; and
Ar is an aromatic-containing moiety.

With respect to beta blockers having a structure encompassed by Formula II, structures of Formula II are defined as follows:

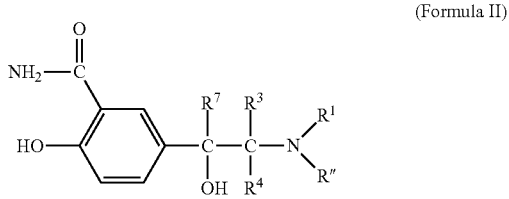

(Formula II)

wherein:
$R^1$ is H or lower alkyl;
R" is selected from the group consisting of an arylalkyl group and an aryloxyalkyl group;
$R^3$ is H or lower alkyl;
$R^4$ is H or lower alkyl; and
$R^7$ is H or lower alkyl.

In one or more embodiments of the invention, a composition is provided, the composition comprising a compound comprising a beta blocker residue covalently attached via a stable or degradable linkage to a water-soluble and non-peptidic oligomer, and optionally, a pharmaceutically acceptable excipient.

In one or more embodiments of the invention, a dosage form is provided, the dosage form comprising a compound comprising a beta blocker residue covalently attached via a stable or degradable linkage to a water-soluble, non-peptidic oligomer, wherein the compound is present in a dosage form.

In one or more embodiments of the invention, a method is provided, the method comprising covalently attaching a water-soluble, non-peptidic oligomer to a beta blocker.

In one or more embodiments of the invention, a method is provided, the method comprising administering a compound comprising a beta blocker residue covalently attached via a stable or degradable linkage to a water-soluble, non-peptidic oligomer.

These and other objects, aspects, embodiments and features of the invention will become more fully apparent to one of ordinary skill in the art when read in conjunction with the following detailed description.

DETAILED DESCRIPTION OF THE INVENTION

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 2 to about 50 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" (also called an oligoethylene glycol) is one in which substantially all (and more preferably all) monomeric subunits are ethylene oxide subunits. The oligomer may, however, contain distinct end capping moieties or functional groups, e.g., for conjugation. Typically, PEG oligomers for use in the present invention will comprise one of the two following structures: "—$(CH_2CH_2O)_n$—" or "—$(CH_2CH_2O)_{n-1}CH_2CH_2$—," depending upon whether the terminal oxygen(s) has been displaced, e.g., during a synthetic transformation. For PEG oligomers, "n" varies from about 2 to 50, preferably from about 2 to about 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. Exemplary end capping groups comprise a $C_{1-5}$ alkyl group, such as methyl, ethyl and benzyl), as well as aryl, heteroaryl, cyclo, heterocyclo, and the like. For the purposes of the present invention, the preferred capping groups have relatively low molecular weights such as methyl or ethyl. The end-capping group can also comprise a detectable label. Such labels include, without limitation, fluorescers, chemiluminescers, moieties used in enzyme labeling, colorimetric labels (e.g., dyes), metal ions, and radioactive moieties.

"Branched", in reference to the geometry or overall structure of an oligomer, refers to an oligomer having two or more polymers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under ordinary physiological conditions. The tendency of a bond to hydrolyze in water under ordinary physiological conditions will depend not only on the general type of linkage connecting two central atoms but also on the substituents attached to these central atoms. Such bonds are generally recognizable by those of ordinary skill in the art. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes under ordinary physiological conditions.

A "stable" linkage or bond refers to a chemical moiety or bond, typically a covalent bond, that is substantially stable in water, that is to say, does not undergo hydrolysis under ordinary physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under ordinary physiological conditions. Hydrolysis rates of representative chemical bonds can be found in most standard chemistry textbooks.

In the context of describing the consistency of oligomers in a given composition, "substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a distribution and would possess a MW/Mn value of 1.0005, and more preferably, a MW/Mn value of 1.0000 if the oligomer were not attached to the beta-blocker residue. A composition comprised of monodisperse conjugates can include, however, one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the beta-blocker residue. A composition comprised of bimodal conjugates can include, however, one or more nonconjugate substances such as solvents, reagents, excipients, and so forth.

A "beta blocker" is broadly used herein to refer to an organic, inorganic, or organometallic compound typically having a molecular weight of less than about 1000 Daltons (and typically less than 500 Daltons) and having some degree of activity as an antagonist at beta 1 receptors. Thus, a beta blocker will oppose or antagonize the excitability of effects of norepinephrine released from sympathetic or beta receptors nerve endings. A beta blocker is also referred to as a beta-adrenergic blocking agent. Beta blockers of the invention encompass oligopeptides and other biomolecules having a molecular weight of less than about 1000 Daltons.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. Unless the context clearly dictates otherwise, the term "biological membrane" does not include those membranes associated with the middle gastro-intestinal tract (e.g., stomach and small intestines).

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

A "reduced rate of metabolism" in reference to the present invention, refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and must pass through the liver prior to reaching the systemic circulation. Because the liver is the primary site of drug metabolism or biotransformation, a substantial amount of drug can be metabolized before it ever reaches the systemic circulation. The degree of first pass metabolism, and thus, any reduction thereof, can be measured by a number of different approaches. For instance, animal blood samples can be collected at timed intervals and the plasma or serum analyzed by liquid chromatography/mass spectrometry for metabolite levels. Other techniques for measuring a "reduced rate of metabolism" associated with the first pass metabolism and other metabolic processes are known in the art, described herein and/or in the relevant literature, and/or can be determined by one of ordinary skill in the art. Preferably, a conjugate of the invention can provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that can be included in the compositions of the invention in order to provide for a composition that has an advantage (e.g., more suited for administration to a patient) over a composition lacking the component and that is recognized as not causing significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

An "aromatic-containing moiety" is a collection of atoms containing at least aryl and optionally one or more atoms. Suitable aromatic-containing moieties are described herein.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a threshold level of active agent and/or conjugate in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, typically, but not necessarily, in the form of a water-soluble oligomer-small molecule drug conjugate, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a beta blocker residue covalently attached via a stable or degradable linkage to a water-soluble, non-peptidic oligomer.

In one or more embodiments of the invention, a compound is provided, the compound comprising a beta blocker residue covalently attached via a stable or degradable linkage to a water-soluble, non-peptidic oligomer, wherein the beta blocker has a structure encompassed by the following formula:

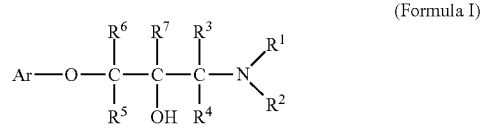

(Formula I)

wherein:

$R^1$ is selected from the group consisting of hydrogen, lower alkyl, lower alkenyl, hydroxy-lower alkenyl, and phenyl-lower alkyl, $R^2$ is selected from the group consisting of hydrogen, alkyl (preferably lower alkyl, such as isopropyl or tertiary butyl), hydroxyalkyl (preferably hydroxyl-lower alkenyl), phenyl alkyl (preferably phenyl-lower alkyl), aralkyl (optionally mono- to tri-substituted by alkyl, alkoxy, OH, F, and/or Cl or monosubstituted with methylenedioxy), alkenyl (preferably lower alkenyl), hydroxyalkenyl (preferably hydroxy-lower alkenyl), cyano, branched cyano, phenyl (optionally substituted with alkyl), halophenyl (optionally substituted with alkyl), alkoxy, alkoxyphenyl, acyl, acylamino, aralkyl, aralkyl wherein the aryl radical is mono- to tri-subsituted by alkyl, alkoxy, OH, F, and/or Cl or mono substituted by methylenedioxy, or $R^1$ and $R^2$ can be joined together with the N to form heterocyclic structure;

$R^3$ is H or lower alkyl;
$R^4$ is H or lower alkyl;
$R^5$ is H or lower alkyl;
$R^6$ is H or lower alkyl;
$R^7$ is H or lower alkyl; and
Ar is an aromatic-containing moiety.

In one or more embodiments of the invention, a compound is provided, the compound comprising a beta blocker residue covalently attached via a stable or degradable linkage to a water-soluble, non-peptidic oligomer, wherein the beta blocker has a structure encompassed by the following formula:

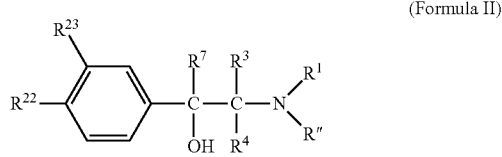

(Formula II)

wherein:

$R^1$ is H or lower alkyl;

R" is selected from the group consisting of an arylalkyl group and an aryloxyalkyl group;

$R^3$ is H or lower alkyl;

$R^4$ is H or lower alkyl;

$R^7$ is H or lower alkyl;

$R^{22}$ is —OH or —NH—SO$_2$—CH$_3$; and $R^{23}$ is H or —C(O)—NH$_2$.

Examples of specific beta blockers include those selected from the group consisting of acebutolol, alprenolol, atenolol, betaxolol, bisoprolol, carteolol, esmolol, labetolol, levobunolol, metoprolol, nadolol, penbutolol, pindolol, propranolol, sotalol and timolol.

It is believed that an advantage of the compounds of the present invention is their ability to retain some degree of beta blocker activity while also exhibiting a decrease in metabolism. Although not wishing to be bound by theory, it is believed that the beta blocker residue- and oligomer-containing compounds described herein—in contrast to the oligomer-free "original" beta blocker structure—are not metabolized as readily because the oligomer serves to reduce the overall affinity of the compound to substrates that can metabolize beta blockers. In addition (and again, not wishing to be bound by theory), the extra size introduced by the oligomer—in contrast to the oligomer-free "original" beta blocker structure—reduces the ability of the compound to cross the blood-brain barrier. Even should the linkage between the residue of the beta blocker and the oligomer be degradable, the compound still offers advantages (such as avoiding first-pass metabolism upon initial absorption).

Use of discrete oligomers (e.g., from a monodisperse or bimodal composition of oligomers, in contrast to relatively impure compositions) to form oligomer-containing compounds can advantageously alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability can be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses can be conducted, for example, by contract research organizations such as Absorption Systems, Exton, Pa.). In one example of the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble, non-peptidic oligomer-small molecule drug compound exhibits a blood-brain barrier crossing rate that is reduced as compared to the crossing rate of the small molecule drug not attached to the water-soluble, non-peptidic oligomer. Preferred exemplary reductions in blood-brain barrier crossing rates for the compounds described herein include reductions of: at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a compound of the invention is at least about 20%.

As indicated above, the compounds of the invention include a beta blocker residue. Assays for determining whether a given compound (regardless of whether the compound includes a water-soluble, non-peptidic oligomer or not) can block beta adrenergic stimuli are described infra.

Exemplary beta blockers have the following formula:

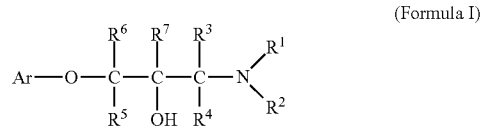

(Formula I)

wherein:

$R^1$ is selected from the group consisting of hydrogen, lower alkyl, lower alkenyl, hydroxy-lower alkenyl, and phenyl-lower alkyl;

$R^2$ is selected from the group consisting of hydrogen, alkyl (preferably lower alkyl, such as isopropyl or tertiary butyl), hydroxyalkyl (preferably hydroxyl-lower alkenyl), C$_{3-6}$ cycloalkyl, phenyl alkyl (preferably phenyl-lower alkyl), aralkyl (optionally mono- to tri-substituted by alkyl, alkoxy, OH, F, and/or Cl or monosubstituted with methylenedioxy), alkenyl (preferably lower alkenyl), hydroxyalkenyl (preferably hydroxy-lower alkenyl), cyano, branched cyano, phenyl (optionally substituted with alkyl), halophenyl (optionally substituted with alkyl), alkoxy, alkoxyphenyl, acyl, acylamino, aralkyl, aralkyl wherein the aryl radical is mono- to tri-substituted by alkyl, alkoxy, OH, F, and/or Cl or mono substituted by methylenedioxy, or $R^1$ and $R^2$ can be joined together with the N to form heterocyclic structure;

$R^3$ is H or lower alkyl;

$R^4$ is H or lower alkyl;

$R^5$ is H or lower alkyl;

$R^6$ is H or lower alkyl;

$R^7$ is H or lower alkyl; and

Ar is an aromatic-containing moiety.

Preferred aromatic-containing moieties are selected from the group consisting of:

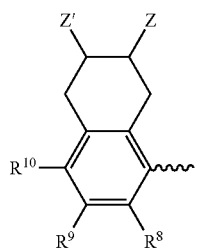

(Formula ArI)

wherein $R^8$ is selected from the group consisting of H, lower alkyl, monocyclic aryl lower alkyl, lower alkoxy, carboxy, and monocyclic cycloalkyl; $R^9$ is selected from the group consisting of H, lower alkyl, monocyclic aryl, lower alkyl, lower alkoxy, carboxy, and monocyclic cycloalkyl; $R^{10}$ is selected from the group consisting of H, lower alkyl, monocyclic aryl, lower alkyl, lower alkoxy, carboxy, and monocyclic $C_{3-6}$ cycloalkyl, and either (i) Z is hydroxyl or alkoxy and Z' is hydroxyl or alkoxy, or (ii) Z and Z' taken together are O< (i.e., Z and Z' together with the carbon atoms to which they are attached form an carbonyl moiety);

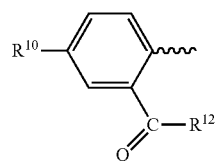

(Formula ArII)

wherein $R^{11}$ is alkanoyl amino of not more than nine carbon atoms and $R''$ is lower alkyl of one through six carbon atoms;

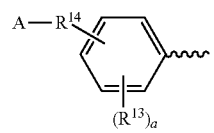

(Formula ArIII)

wherein $R^{14}$ is an electronegative radical (such as alkanoyl of up to 6 carbon atoms, carbamoyl or carbazoyl, or alkylcarbamoyl, or alkenylcarbamoyl or cyano, each of up to 7 carbon atoms), A is an alkyl or alkenyl, (a) is one or two, $R''$ is (in each occurrence independently) selected from the group consisting of hydrogen, halo, alkyl, cycloalkyl, alkenyl, nitro, hydroxyl, alkylthio, alkoxy, alkenyloxy, aryl, aryloxy, aralkyl, aralkoxy, hydroxyalkyl, alkoxyalkyl, haloalkyl, acyl, alkoxycarbonyl, and cyano-containing radicals, and esters and aldehyde condensation products of each of the foregoing;

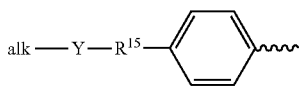

(Formula ArIV)

wherein alk is $C_{1-4}$ alkyl substituted by a 3 to 6 membered cycloalkyl group, Y is —O—, —S—, or —$SO_2$—, and $R^{15}$ is alkylene or alkyleneoxy [e.g., —$(CH_2)_{1-4}$—$(O)_{0-1}$—];

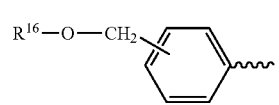

(Formula ArV)

wherein $R^{16}$ is selected from the group consisting of alkenyl, alkynyl, alkoxyalkyl, and alkenyloxyalkyl with 2-6 carbon atoms in each case or cycloalkyl with 3-8 carbon atoms;

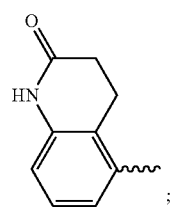

(Formula ArVI)

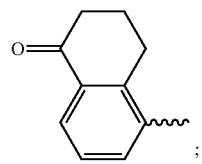

(Formula ArVII)

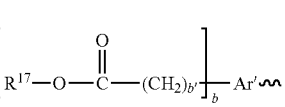

(Formula ArVIII)

wherein Ar' is unsubstituted aromatic or aromatic substituted with lower alkyl, lower alkenyl, lower alkynyl, lower alkoxy, halo, acetamido, amino, nitro, lower alkylamino, hydroxy, lower hydroxylalkyl, cyano, (b) is an integer from 1 to 3, (b'), in each occurrence, is independently an integer of 0 through 10, and $R^{17}$, in each occurrence, is independently lower alkyl, lower cycloalkyl, lower alkenyl, lower alkyl carboxymethyl, aryl carboxymethyl, lower haloalkyl, aralkyl, or aryl;

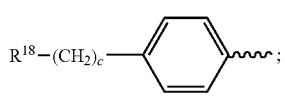

(Formula ArIX)

wherein (c) is one, two or three, and $R^{18}$ is selected from the group consisting of —OR''', —SR''' and —NH—COOR''', R''' being a straight or branched lower alkyl having 1 to 3 carbon atoms;

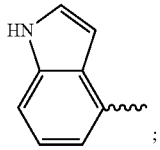
(Formula ArX)

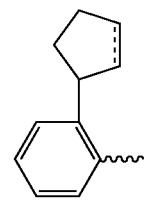
(Formula ArXI)

wherein the dash line represents an optional double bond;

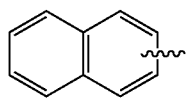
(Formula ArXII)

wherein the naphthalene nucleus optionally bears one or more additional substituents selected from the group consisting of halo, alkyl, alkoxy, and acyl;

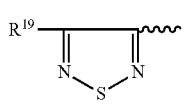
(ArXIII)

wherein $R^{19}$ is selected from the group consisting of H, halo, lower alkyl, lower alkenyl, carbamoyl, cycloalkyl, alkoxy, phenyl, substituted phenyl, amino, and heterocyclic; and

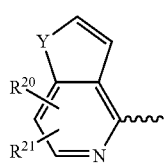
(Formula ArXIV)

wherein Y is —NH—, —S— or —O—, $R^{20}$ is selected from the group consisting of hydrogen, alkyl, halo, nitro, cyano and —COOC$_{1-4}$alkyl, and $R^{21}$ is selected from the group consisting of hydrogen, alkyl, halo, nitro, cyano and —COOC$_{1-4}$alkyl.

In one or more embodiments, the beta blocker is encompassed by the following structure:

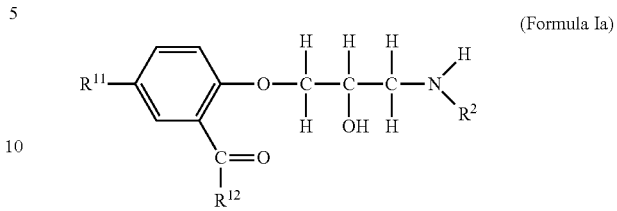
(Formula Ia)

wherein $R^2$ is preferably, with respect to Formula Ia, an alkyl group (including a cycloalkyl groups) of from three to six carbon atoms, $R^{11}$ is alkanoyl amino of not more than nine carbon atoms (preferably not more than six carbon atoms), and $R^{12}$ is an alkyl group of from one to six carbon atoms.

In one or more embodiments, the beta blocker is acebutolol, which has the following structure:

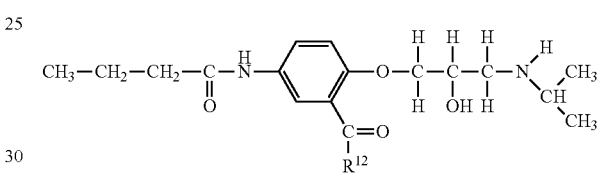

Beta blockers encompassed by Formula Ia can be prepared according to known methods. See, for example, U.S. Pat. No. 3,857,952 for a description of one or more methods for preparing beta blockers encompassed by or related to compounds having structures encompassed by Formula Ia.

In one or more embodiments, the beta blocker is encompassed by the following structure:

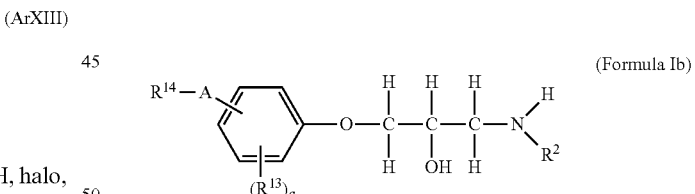
(Formula Ib)

wherein $R^2$ is preferably, with respect to Formula Ib, alkyl or hydroxyalkyl (preferably, with respect to Formula Ib, alkyl or hydroxyalkyl each of up to six carbon atoms), $R^{14}$ is an electronegative radical (such as alkanoyl of up to 6 carbon atoms, carbamoyl or carbazoyl, or alkylcarbamoyl, or alkenylcarbamoyl or cyano, each of up to 7 carbon atoms), A is an alkylene or alkenylene radical, (a) is one or two, $R^{13}$ is (in each occurrence independently) selected from the group consisting of hydrogen, halo, alkyl, cycloalkyl, alkenyl, nitro, hydroxyl, alkylthio, alkoxy, alkenyloxy, aryl, aryloxy, aralkyl, aralkoxy, hydroxyalkyl, alkoxyalkyl, haloalkyl, acyl, alkoxycarbonyl, and cyano-containing radicals, and esters and aldehyde condensation products of each of the foregoing. In one or more embodiments, the beta blocker is atenolol, which has the following structure:

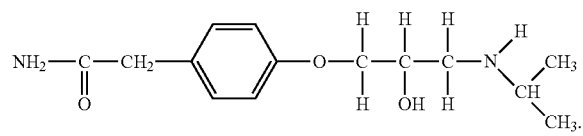 [SMILES: CC(C)NCC(O)COc1ccc(CC(N)=O)cc1]

Beta blockers encompassed by Formula Ib can be prepared according to known methods. See, for example, U.S. Pat. Nos. 3,663,607 and 3,836,671 for a description of one or more methods for preparing beta blockers encompassed by or related to compounds having structures encompassed by Formula Ib.

In one or more embodiments, the beta blocker is encompassed by the following structure:

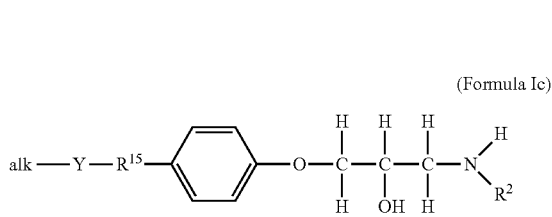

(Formula Ic)

wherein $R^2$ is preferably, with respect to Formula Ic, selected from the group consisting of branched $C_{3-4}$ alkyl, $C_{3-4}$ cycloalkyl, branched cyano($C_{3-4}$ alkyl), phenyl ($C_{2-3}$ alkyl), halophenyl($C_{2-3}$ alkyl), ($C_{1-4}$ alkoxy)phenyl($C_{2-4}$ alkyl) and ($C_{1-4}$ acyl)amino($C_{1-4}$ alkyl), alk is $C_{1-4}$ alkyl substituted by a 3 to 6 membered cycloalkyl group, Y is —O—, —S—, or —SO$_2$—, and $R^{15}$ is alkylene or alkyleneoxy [e.g., —(CH$_2$)$_{1-4}$—(O)$_{0-1}$—]. In one or more embodiments, the beta blocker is betaxolol, which has the following structure:

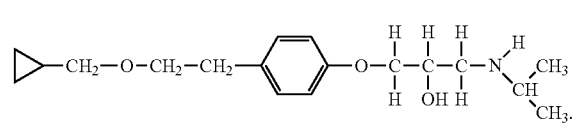

Beta blockers encompassed by Formula Ic can be prepared according to known methods. See, for example, U.S. Pat. No. 4,252,984 for a description of one or more methods for preparing beta blockers encompassed by or related to compounds having structures encompassed by Formula Ic.

In one or more embodiments, the beta blocker is encompassed by the following structure:

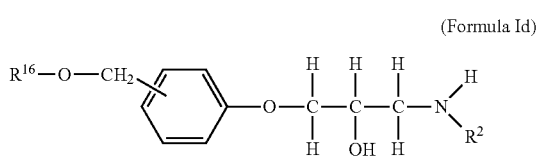

(Formula Id)

wherein $R^2$ is preferably, with respect to Formula Id, selected from the group consisting of $C_{1-6}$ alkyl, hydroxyl ($C_{1-6}$alkyl), $C_{3-8}$ cycloalkyl, aralkyl, aralkyl wherein the aryl radical is mono- to tri-substituted by alkyl, alkoxy, OH, F and/or Cl or mono-substituted by methylenedioxy, and $R^{16}$ is selected from the group consisting of alkenyl, alkynyl, alkoxyalkyl, and alkenyloxyalkyl with 2-6 carbon atoms in each case or cycloalkyl with 3-8 carbon atoms. In one or more embodiments, the beta blocker is bisoprolol, which has the following structure:

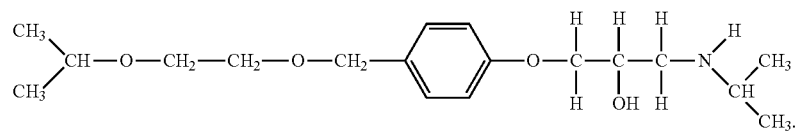

Beta blockers encompassed by Formula Id can be prepared according to known methods. See, for example, U.S. Pat. No. 4,258,062 for a description of one or more methods for preparing beta blockers encompassed by or related to compounds having structures encompassed by Formula Id.

In one or more embodiments, the beta blocker is encompassed by the following structure:

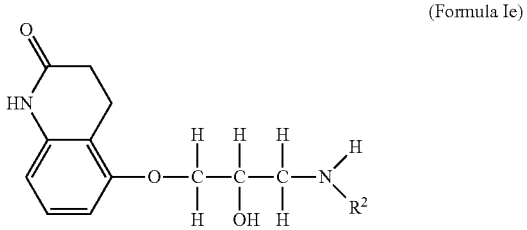

(Formula Ie)

wherein $R^2$ is preferably, with respect to Formula Ie, selected from the group consisting of straight chain $C_{1-4}$ alkyl and branched chain $C_{1-4}$ alkyl. In one or more embodiments, the beta blocker is carteolol, which has the following structure:

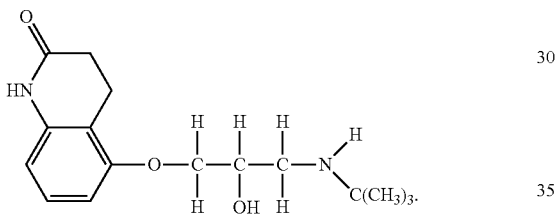

Beta blockers encompassed by Formula Ie can be prepared according to known methods. See, for example, U.S. Pat. No. 3,910,924 for a description of one or more methods for preparing beta blockers encompassed by or related to compounds having structures encompassed by Formula Ie.

In one or more embodiments, the beta blocker is encompassed by the following structure:

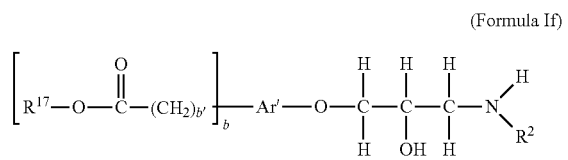

(Formula If)

wherein $R^2$ is preferably, with respect to Formula If, selected from the group consisting of lower alkyl and aralkyl, Ar' is unsubstituted aromatic or aromatic substituted with lower alkyl, lower alkenyl, lower alkynyl, lower alkoxy, halo, acetamido, amino, nitro, lower alkylamino, hydroxyl, lower hydroxylalkyl, cyano, (b) is an integer from 1 to 3, (b'), in each occurrence, is independently an integer of 0 through 10, and $R^{17}$, in each occurrence, is independently selected from the group consisting of lower alkyl, lower cycloalkyl, lower alkenyl, lower alkyl carboxymethyl, aryl carboxymethyl, lower haloalkyl, aralkyl, or aryl. In one or more embodiments, the beta blocker is esmolol, which has the following structure:

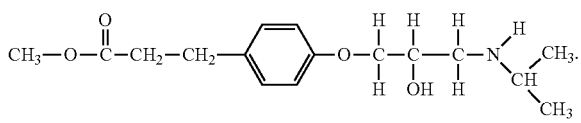

Beta blockers encompassed by Formula If can be prepared according to known methods. See, for example, U.S. Pat. No. 4,593,119 for a description of one or more methods for preparing beta blockers encompassed by or related to compounds having structures encompassed by Formula If.

In one or more embodiments, the beta blocker is encompassed by the following structure:

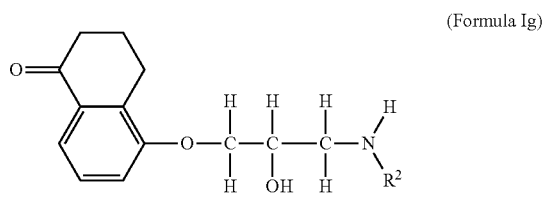

(Formula Ig)

wherein $R^2$ is preferably, with respect to Formula Ig, selected from the group consisting of alkyl, aralkyl, and heteroarylalkyl. In one or more embodiments, the beta blocker is levobunolol, which has the following structure:

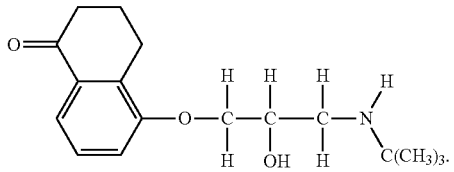 [SMILES: CC(C)(C)NCC(O)COc1cccc2c1CCCC2=O]

Beta blockers encompassed by Formula Ig can be prepared according to known methods. See, for example, U.S. Pat. Nos. 3,649,691 and 4,463,176 for a description of one or more methods for preparing beta blockers encompassed by or related to compounds having structures encompassed by Formula Ig.

In one or more embodiments, the beta blocker is encompassed by the following structure:

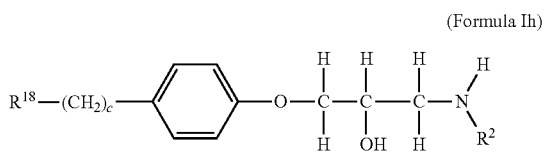

(Formula Ih)

wherein $R^2$ is preferably, with respect to Formula Ih, alkyl (such as isopropyl or t-butyl), (c) is one, two or three, and $R^{18}$ is selected from the group consisting of —OR''', —SR''' and —NH—COOR''', R''' being a straight or branched lower alkyl radical having 1 to 3 carbon atoms. In one or more embodiments, the beta blocker is metoprolol, which has the following structure:

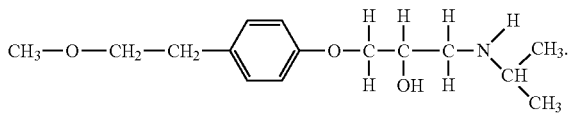

Beta blockers encompassed by Formula Ih can be prepared according to known methods. See, for example, U.S. Pat. No. 3,873,600 for a description of one or more methods for preparing beta blockers encompassed by or related to compounds having structures encompassed by Formula Ih.

In one or more embodiments, the beta blocker is encompassed by the following structure:

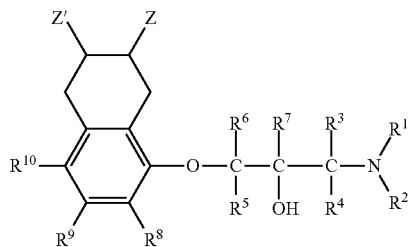

(Formula Ii)

wherein: either (a) $R^1$ is preferably, with respect to Formula Ii, selected from the group consisting of hydrogen, lower alkyl, lower alkenyl, hydroxy-lower alkenyl, and phenyl-lower alkyl and $R^2$ is preferably, with respect to Formula Ii, selected from the group consisting of hydrogen, lower alkyl, lower alkenyl, hydroxy-lower alkenyl, and phenyl-lower alkyl, or (b) $R^1$ and $R^2$ are joined together with the N to which they are attached to form a heterocycle; $R^3$ is H or lower alkyl; $R^4$ is H or lower alkyl; $R^5$ is H or lower alkyl; $R^6$ is H or lower alkyl; $R^7$ is H or lower alkyl; $R^8$ is selected from the group consisting of H, lower alkyl, monocyclic aryl lower alkyl, lower alkoxy, carboxy, and monocyclic cycloalkyl; $R^9$ is selected from the group consisting of H, lower alkyl, aryl, lower alkyl, lower alkoxy, carboxy, and cycloalkyl; $R^{10}$ is selected from the group consisting of H, lower alkyl, monocyclic aryl, lower alkyl, lower alkoxy, carboxy, and monocyclic cycloalkyl, and either (i) Z is hydroxyl or alkoxy and Z' is hydroxyl or alkoxy, or (ii) Z and Z' taken together are O<. In one or more embodiments, the beta blocker is nadolol, which has the following structure:

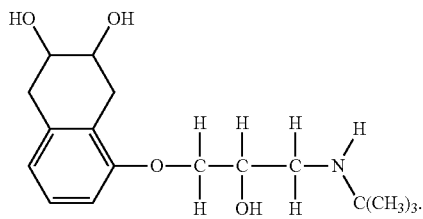 [SMILES: CC(C)(C)NCC(O)COc1cccc2c1CC(O)C(O)C2]

Beta blockers encompassed by Formula Ii can be prepared according to known methods. See, for example, U.S. Pat. No. 3,935,267 for a description of one or more methods for preparing beta blockers encompassed by or related to compounds having structures encompassed by Formula Ii.

In one or more embodiments, the beta blocker is encompassed by the following structure:

(Formula Ij)

wherein $R^2$ is preferably, with respect to Formula Ij, selected from the group consisting of branched alkyl and cycloalkyl, and the dashed line represents an optional double bond. In one or more embodiments, the beta blocker is penbutolol, which has the following structure:

Beta blockers encompassed by Formula Ij can be prepared according to known methods. See, for example, U.S. Pat. No. 3,551,493 for a description of one or more methods for preparing beta blockers encompassed by or related to compounds having structures encompassed by Formula Ij.

In one or more embodiments, the beta blocker is encompassed by the following structure:

(Formula Ik)

wherein $R^2$ is preferably, with respect to Formula Ik, selected from the group consisting of alkyl, cycloalkyl, hydroxyalkyl and phenoxyalkyl, Y is —NH—, —S— or —O—, $R^{20}$ is selected from the group consisting of hydrogen, alkyl, halo, nitro, cyano and —COOC$_{1-4}$alkyl, and $R^{21}$ is selected from the group consisting of hydrogen, alkyl, halo, nitro, cyano and —COOC$_{1-4}$alkyl. In one or more embodiments, the beta blocker is pindolol, which has the following structure:

Beta blockers encompassed by Formula Ik can be prepared according to known methods. See, for example, U.S. Pat. No. 3,998,835 for a description of one or more methods for preparing beta blockers encompassed by or related to compounds having structures encompassed by Formula Ik.

In one or more embodiments, the beta blocker is encompassed by the following structure:

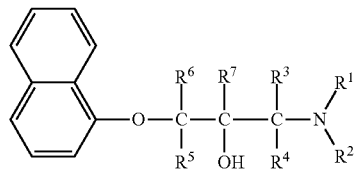

(Formula Il)

wherein $R^1$ is preferably, with respect to Formula Il, selected from the group consisting of hydrogen, alkyl, cycloalkyl, alkenyl and aralkyl, $R^2$ is preferably, with respect to Formula Il, selected from the group consisting of hydrogen, alkyl, cycloalkyl, alkenyl and aralkyl, $R^3$ is H or lower alkyl, $R^4$ is H or lower alkyl, $R^5$ is H or lower alkyl, $R^6$ is H or lower alkyl, and $R^7$ is H or lower alkyl. In one or more embodiments, the beta blocker is propranolol, which has the following structure:

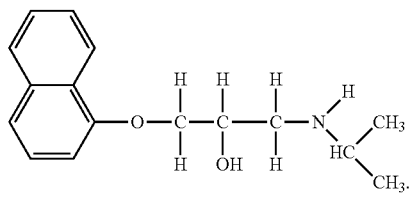 [SMILES: CC(C)NCC(O)COc1cccc2ccccc12]

Beta blockers encompassed by Formula Il can be prepared according to known methods. See, for example, U.S. Pat. Nos. 3,337,628 and 3,520,919 for a description of one or more methods for preparing beta blockers encompassed by or related to compounds having structures encompassed by Formula Il.

In one or more embodiments, the beta blocker is encompassed by the following structure:

(Formula Im)

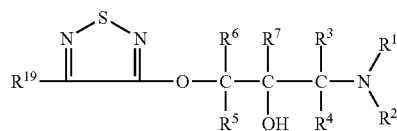

wherein $R^1$ is preferably, with respect to Formula Im, selected from the group consisting of hydrogen, alkyl, cycloalkyl, alkenyl and aralkyl, $R^2$ is preferably, with respect to Formula Im, selected from the group consisting of hydrogen, alkyl, cycloalkyl, alkenyl and aralkyl, $R^3$ is H or lower alkyl, $R^5$ is H or lower alkyl, $R^6$ is H or lower alkyl, $R^7$ is H or lower alkyl, and $R^{19}$ is selected from the group consisting of H, halo, lower alkyl, lower alkenyl, carbamoyl, cycloalkyl, alkoxy, phenyl, substituted phenyl, amino, and heterocyclic (e.g., morpholinyl). In one or more embodiments, the beta blocker is timolol, which has the following structure:

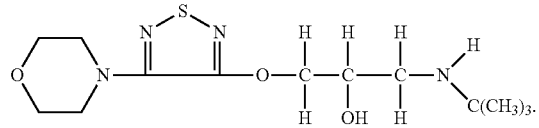 [SMILES: CC(C)(C)NCC(O)COc1nsnc1N1CCOCC1]

Beta blockers encompassed by Formula Im can be prepared according to known methods. See, for example, U.S. Pat. Nos. 3,655,663 and 3,657,237 for a description of one or more methods for preparing beta blockers encompassed by or related to compounds having structures encompassed by Formula Im.

Further exemplary beta blockers have the following formula (Formula II)

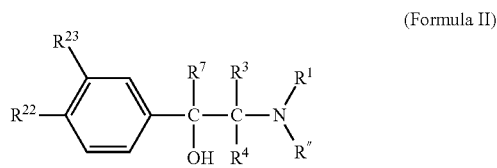

wherein: $R^1$ is H or lower alkyl; $R''$ is selected from the group consisting of an arylalkyl group and an aryloxyalkyl group (preferably wherein with respect to arylalkyl group, the alkyl portion contains from one to six carbon atoms and the aryl portion of which may be substituted by one or more alkoxy groups or hydroxyl groups, and preferably wherein with respect to the aryloxylalkyl group, the alkyl portion contains from one to six carbon atoms and the aryloxy portion is substituted with one or more alkoxy or hydroxyl groups); $R^3$ is H or lower alkyl; $R^4$ is H or lower alkyl; $R^7$ is H or lower alkyl; $R^{22}$ is —OH or —NH—$SO_2$—$CH_3$; and $R^{23}$ is H or —C(O)—$NH_2$. In one or more embodiments, the beta blocker is labetolol, which has the following structure:

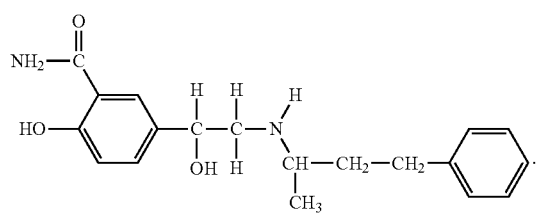 [SMILES: CC(CCc1ccccc1)NCC(O)c1ccc(O)c(C(N)=O)c1]

In one or more embodiments, the beta blocker is sotalol, which has the following structure:

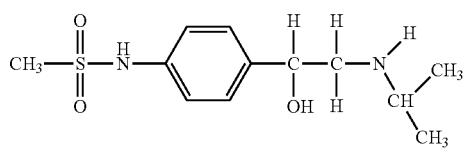

Beta blockers encompassed by Formula II can be prepared according to known methods. See, for example, U.S. Pat. No. 4,012,444 and Uloth et al. (1966) J. Med. Chem.

9:88 for a description of one or more methods for preparing beta blockers encompassed by or related to compounds having structures encompassed by Formula II.

In some instances, beta blockers can be obtained from commercial sources. In addition, beta blockers can be obtained through chemical synthesis. Examples of beta blockers as well as synthetic approaches for preparing beta blockers are described in the literature and in, for example, U.S. Pat. Nos. 3,857,952, 3,663,607, 3,836,671, 4,252,984, 4,258,062, 3,910,924, 4,593,119, 4,012,444, 3,649,691, 4,463,176, 3,873,600, 3,935,267, 3,551,493, 3,998,835, 3,520,919, 3,337,628, 3,520,919, 3,655,663, 3,657,237, in Swiss Patent Nos. 472,404 and 469,002, and in Uloth et al. (1966) *J. Med. Chem.* 9:88.

Each of these (and other) beta blockers can be covalently attached (either directly or through one or more atoms) to a water-soluble and non-peptidic oligomer.

Small molecule drugs useful in the invention generally have a molecular weight of less than 1000 Da. Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The beta blocker for coupling to a water-soluble, non-peptidic oligomer possesses a free hydroxyl, carboxyl, thio, amino group, or the like (i.e., "handle") suitable for covalent attachment to the oligomer. In addition, the beta blocker can be modified by introduction of a reactive group, preferably by conversion of one of its existing functional groups to a functional group suitable for formation of a stable covalent linkage between the oligomer and the drug. Both approaches are illustrated in the Experimental section.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, it can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble and non-peptidic polymer includes $CH_3—(OCH_2CH_2)_n—$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20;

between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the beta blocker (in contrast to the step-wise addition of one or more monomers to effectively "grow" the oligomer onto the beta blocker), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble and non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble and non-peptidic polymer is attached to the beta blocker) may be a single bond, a single atom, such as an oxygen atom or a sulfur atom, two atoms, or a number of atoms. A spacer moiety is typically but is not necessarily linear in nature. The spacer moiety, "X," is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety of the invention, X, may be any of the following: "-" (i.e., a covalent bond, that may be stable or degradable, between the beta blocker residue and the water-soluble, non-peptidic oligomer), —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—C(O)—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

The linkage "X" between the water-soluble, non-peptidic oligomer and the small molecule is typically formed by reaction of a functional group on a terminus of the oligomer (or nascent oligomer when it is desired to "grow" the oligomer onto the beta blocker) with a corresponding functional group within the beta blocker. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N═C═O) on a drug, or vice versa, forms a urea linkage (R—NH—(C═O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: $CH_3O-(CH_2-CH_2-O)_n-(CH_2)_p-C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, all but one termini of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NETS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(═O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N═C═O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the beta blocker may not have a functional group suited for conjugation. In this instance, it is possible to modify (or "functionalize") the "original" beta blocker so that it does have a functional group suited for conjugation. For example, if the beta blocker has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule beta blocker bearing a carboxyl group wherein the carboxyl group-bearing small molecule beta blocker is coupled to an amino-terminated oligomeric ethylene glycol, to provide a conjugate having an amide group covalently linking the small molecule beta blocker to the oligomer. This can be performed, for example, by combining the carboxyl group-bearing small molecule beta blocker with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule beta blocker bearing a hydroxyl group wherein the hydroxyl group-bearing small molecule beta blocker is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule beta blocker bearing a ketone group by first reducing the ketone group to form the corresponding hydroxyl group. Thereafter, the small molecule beta blocker now bearing a hydroxyl group can be coupled as described herein.

In still another instance, it is possible to prepare a conjugate of a small molecule beta blocker bearing an amine group. In one approach, the amine group-bearing small molecule beta blocker and an aldehyde-bearing oligomer are dissolved in a suitable buffer after which a suitable reducing agent (e.g., $NaCNBH_3$) is added. Following reduction, the result is an amine linkage formed between the amine group of the amine group-containing small molecule beta blocker and the carbonyl carbon of the aldehyde-bearing oligomer.

In another approach for preparing a conjugate of a small molecule beta blocker bearing an amine group, a carboxylic acid-bearing oligomer and the amine group-bearing small molecule beta blocker are combined, typically in the presence of a coupling reagent (e.g., DCC). The result is an amide linkage formed between the amine group of the amine group-containing small molecule beta blocker and the carbonyl of the carboxylic acid-bearing oligomer.

Exemplary conjugates of the beta blockers of Formula I include those having the following structure:

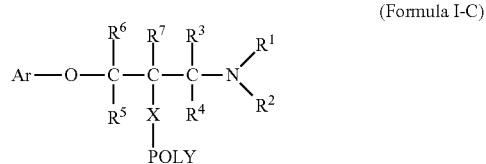

(Formula I-C)

wherein each of $R^1$, $R^2$, $R^3$, $R^4$, $R^5$, $R^6$, $R^7$, and Ar is as previously defined with respect to Formula I, X is a spacer moiety, and POLY is a water-soluble, non-peptidic oligomer.

Further exemplary conjugates of the beta blockers of Formula II include those having the following structure:

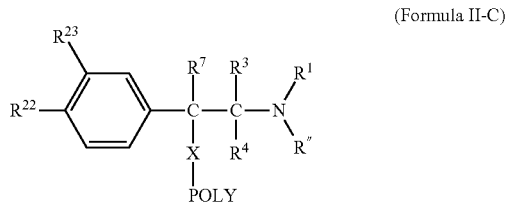

(Formula II-C)

Wherein each of $R^1$, $R''$, $R^3$, $R^4$, $R^7$, $R^{22}$ and $R^{23}$ is as previously defined with respect to Formula I, X is a spacer moiety, and POLY is a water-soluble, non-peptidic oligomer.

The conjugates of the invention can exhibit a reduced blood-brain barrier crossing rate. Moreover, the conjugates maintain at least about 5%, 10%, 20%, 30%, 40%, 50%, 60%, 70%, or more of the bioactivity of the unmodified parent small molecule drug.

While it is believed that the full scope of the conjugates disclosed herein behave as described, an optimally sized oligomer can be identified as follows.

First, an oligomer obtained from a monodisperse or bimodal water soluble oligomer is conjugated to the small molecule drug. Preferably, the drug is orally bioavailable, and on its own, exhibits a non-negligible blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. Preferably, the compounds according to the invention maintain a significant degree of bioactivity relative to the parent drug, i.e., greater than about 30% of the bioactivity of the parent drug, or even more preferably, greater than about 50% of the bioactivity of the parent drug.

The above steps are repeated one or more times using oligomers of the same monomer type but having a different number of subunits and the results compared.

For each conjugate whose ability to cross the blood-brain barrier is reduced in comparison to the non-conjugated small molecule drug, its oral bioavailability is then assessed. Based upon these results, that is to say, based upon the comparison of conjugates of oligomers of varying size to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible and allows one to effectively tailor the properties of the resulting conjugate. By making small, incremental changes in oligomer size and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

To determine whether the beta blocker or the conjugate of a beta blocker and a water-soluble non-peptidic polymer has activity as a beta adrenergic antagonist, it is possible to test such a compound. With respect to beta-2 adrenergic activity, for example, human promyelocytic leukemia cells (HL-60 cells) can be washed and added to physiological buffer. The compound of interest or an antagonist control (such as propranolol) is added. Thereafter, 100 nM (final) isoproterenol is added. After twenty minutes at room temperature, cells are centrifuged, buffer removed, and 0.1M HCl is added to stop reaction. EIA is performed and alkaline phosphatase activity is read at 405 nm as the detection agent. See Seifert et al. (1992) Eur. J. Biochem. 203(1-2):143-151 and Klinker et al. (1996) Gen. Pharmacol. 27(1):33-54.

With respect to beta-1 adrenergic activity, human recombinant/Sf9 cells can be used wherein reactions are carried out in 50 mM HEPES [pH 7.4] containing 3 mM $MgCl_2$, 0.1 µM GDP, 10 µM GDP, 10 µg/mL saponin, and 1 mM DTT (diothiothreitol). The compound of interest is added to the membrane and then incubated for ten minutes. Thereafter, 100 nM GTP-Eu is added and incubated for an additional thirty minutes. Europium fluorescence is measured in a time-resolved fluorometer in order to ascertain any functional antagonist activity at the adrenergic beta 1 site. See Frang et al. (2003) Assay and Drug Development Technology 1(2): 275-280, and Minneman et al. (1979) Mol. Pharmacol. 16:34-46.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3rd Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (*theobroma* oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism) can be reduced, the conjugates are particularly useful when the small molecule drug is metabolized by a hepatic enzyme (e.g., one or more of the cytochrome P450 isoforms) and/or by one or more intestinal enzymes.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by a NMR spectrometer manufactured by Bruker (MHz ≥300). A list of certain compounds as well as the source of the compounds is provided below.

Example 1

Preparation of Propranolol Conjugate A

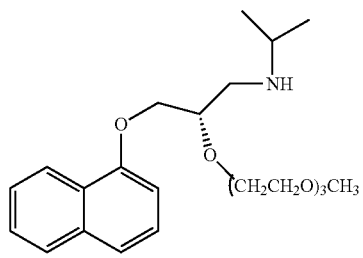

"Propranolol Conjugate A"

Into a 100 mL flask was placed 60% sodium hydride (0.40 g, 0.01 mol), and washed with hexanes (3×2 mL). The residual hexanes were removed under vacuum. The residue was taken up in anhydrous THF (10 mL). Propranolol hydrochloride (0.50 g, 1.69 mmol) in THF (10 mL) was then added all at once, followed by mPEG$_3$-bromide (0.77 g, 3.38 mmol, 2.0 equivalents) in THF (15 mL). The cloudy mixture was stirred under nitrogen and heated to 45° C. After 22 hours the reaction was stopped. The mixture was concentrated under reduced pressure, and then purified by Biotage chromatography (40+M cartridge; 0 to 5% methanol/dichloromethane gradient). Obtained 0.45 g (66%) of Propranolol Conjugate A as a yellow oil. 98% purity (HPLC). Structure confirmed by $^1$H NMR.

Example 2

Preparation of Propranolol Conjugate B

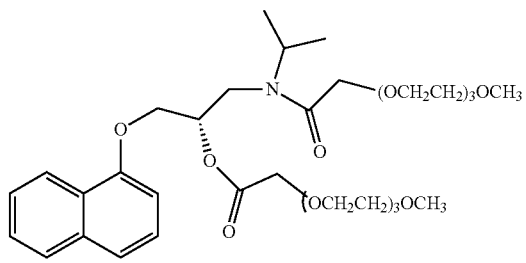

"Propranolol Conjugate B"

Into a 100 mL flask was placed propranolol hydrochloride (0.50 g, 1.69 mmol), mPEG$_3$-CM (2.25 g, 10.1 mmol, 6.0 equivalents), triethylamine (0.47 mL, 3.38 mmol, 2.0 equivalents), DMAP (0.12 g, 1.01 mmol, 0.6 equivalents) and dichloromethane (45 mL). The solution was stirred under nitrogen and cooled to 0° C. Then DCC (1.0 M in DCM) (3.38 mL, 3.38 mmol, 2.0 equivalents) was added at 0° C., and then the temperature was allowed to equilibrate to room temperature. After 20 hours, the reaction mixture was filtered through celite. The filtrate was concentrated under reduced pressure, and the residue purified by Biotage chromatography. (40+M cartridge; 0 to 5% methanol/dichloromethane gradient). Obtained 0.52 g, (47%) of Propranolol Conjugate B as a sticky solid. 95% purity (HPLC). Structure confirmed by $^1$H NMR.

Example 3

Preparation of Propranolol Conjugate C

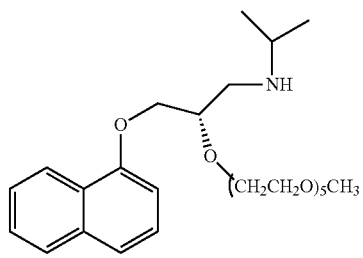

"Propranolol Conjugate C"

Into a 100 mL flask was placed 60% sodium hydride (0.41 g, 0.01 mol), and washed with hexanes (4×2 mL). The residual hexanes were removed under vacuum. The residue was taken up in anhydrous THF (10 mL). Propranolol hydrochloride (0.50 g, 1.69 mmol) in THF (10 mL) was then added all at once, followed by m-PEG-5-bromide (1.07 g, 3.38 mmol, 2.0 equivalents) in THF (15 mL). The cloudy mixture was stirred under nitrogen and heated to 45° C. After 20 hours the reaction was stopped. The mixture was concentrated under reduced pressure, and then purified by Biotage chromatography (40+M cartridge; 0 to 5% methanol/dichloromethane gradient). Obtained 0.67 g (81%) of Propranolol Conjugate C as a light yellow oil. 98% purity (HPLC). Structure confirmed by $^1$H NMR.

Example 4

Preparation of Propranolol Conjugate D

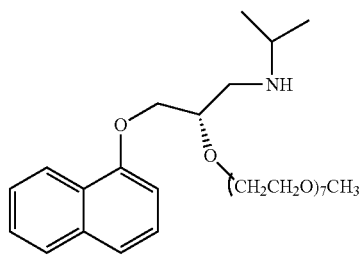

"Propranolol Conjugate D"

Into a 100 mL flask was placed 60% sodium hydride (0.40 g, 0.01 mol), and washed with hexanes (4×2 mL). The residual hexanes were removed under vacuum. The residue was taken up in anhydrous THF (10 mL). Propranolol hydrochloride (0.50 g, 1.69 mmol) in THF (10 mL) was then added all at once, followed by m-PEG-7-bromide (1.36 g, 3.38 mmol, 2.0 equivalents) in THF (15 mL). The cloudy mixture was stirred under nitrogen and heated to 45° C. After 22 hours the reaction was stopped. The mixture was concentrated under reduced pressure, and then purified by Biotage chromatography (40+M cartridge; 0 to 5% methanol/dichloromethane gradient). Obtained 0.68 g (69%) of Propranolol Conjugate D as a light yellow oil. 99% purity (HPLC). Structure confirmed by $^1$H NMR.

Example 5

Preparation of Propranolol Conjugate E

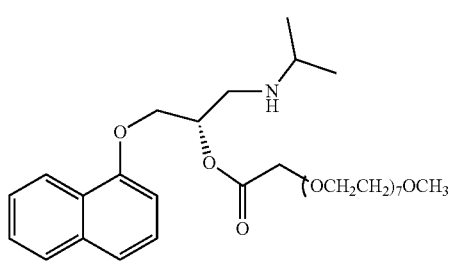

"Propranolol Conjugate E"

Into a 100 mL flask was placed propranolol hydrochloride (0.50 g, 1.69 mmol), m-PEG-7-CM (0.73 g, 1.85 mmol, 1.1 equivalents), triethylamine (294 µL, 2.11 mmol, 1.25 equivalents), DMAP (0.13 g, 1.08 mmol, 0.6 equivalents) and dichloromethane (34 mL). The solution was stirred under nitrogen and cooled to 0° C. Then, DCC (1.0 M in DCM) (3.38 mL, 3.38 mmol, 2.0 equivalents) was added at 0° C., and then the temperature was allowed to equilibrate to room temperature. After 20 hours, the reaction mixture was filtered through celite. The filtrate was concentrated under reduced pressure, and the residue purified by Biotage chromatography. (40+M cartridge; 0 to 5% methanol/dichloromethane gradient). Obtained 0.73 g, (68%) of Propranolol Conjugate E as a clear oil. 98% purity (HPLC). Structure confirmed by $^1$H NMR.

Example 6

Preparation of Propranolol Conjugate F

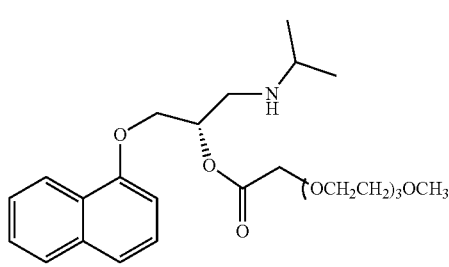

"Propranolol Conjugate F"

Into a 100 mL flask was placed propranolol hydrochloride (0.60 g, 2.31 mmol), m-PEG-3-CM (0.57 g, 2.54 mmol, 1.1 equivalents), triethylamine (354 µL, 2.54 mmol, 1.1 equivalents), DMAP (0.17 g, 1.38 mmol, 0.6 equivalents) and dichloromethane (47 mL). The solution was stirred under nitrogen and cooled to 0° C. Then, DCC (1.0 M in DCM) (4.6 mL, 4.6 mmol, 2.0 equivalents) was added at 0° C., and then the temperature was allowed to equilibrate to room temperature. After 24 hours, the reaction mixture was filtered through celite. The filtrate was concentrated under reduced pressure, and the residue purified by Biotage chromatography. (40+M cartridge; 0 to 5% methanol/dichloromethane gradient). Obtained 0.42 g, (45%) of Propranolol Conjugate F as a light-yellow oil. 98% purity (HPLC). Structure confirmed by $^1$H NMR.

Example 7

Preparation of Timolol Conjugate A

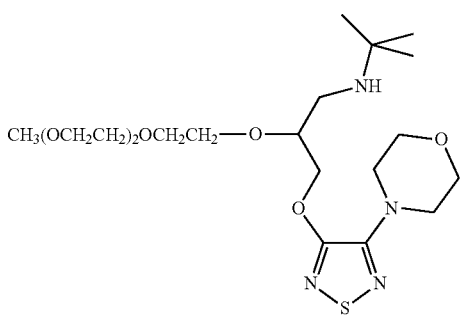

"Timolol Conjugate A"

Timolol (0.4 mmol, 140.0 mg), was dissolved in 5 ml anhydrous THF. Sodium hydride (60% dispersion in mineral oil) (0.8 mmol, 52.8 mg) was added to the timolol solution and the solution was stirred at room temperature for ten minutes. mPEG$_3$-Br (1.4 equivalents) was dissolved in 0.50 ml THF and this solution was added to reaction mixture. The reaction mixture was stirred 16 hours at room temperature. The reaction mixture was washed with an excess amount of saturated ammonium chloride solution and the product was extracted in dichloromethane (3×50 mL). The organic phases were combined and the solvent was removed under reduced pressure. The resulting crude product was purified with Biotage flash chromatography (MeOH/CH$_2$Cl$_2$=40: 1~15:1). The solution was concentrated and dried in vacuo to give a clear gel (~75% yield). HPLC (C-18, 0.1% TFA/milliQ, 0.1-10% acetonitrile) showed purity of 97.06%. $^1$H NMR (CDCl$_3$) confirmed desired product and purity. LC-MS further confirmed the desired product, Timolol Conjugate A, calculated molecular weight of 462.6 and observed molecular weight of 462.

Example 8

Preparation of Timolol Conjugate B

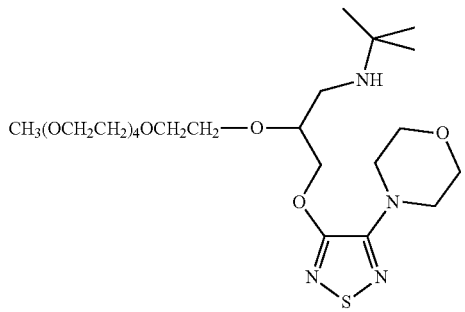

"Timolol Conjugate B"

Timolol (0.4 mmol, 140.0 mg), was dissolved in 5 ml anhydrous THF. Sodium hydride (60% dispersion in mineral oil) (0.8 mmol, 52.8 mg) was added to the timolol solution and the solution was stirred at room temperature for ten minutes. mPEG$_5$-Br (1.4 equivalents) was dissolved in 0.50 ml THF and this solution was added to reaction mixture. The reaction mixture was stirred 16 hours at room temperature. The reaction mixture was washed with an excess amount of saturated ammonium chloride solution and the product was extracted in dichloromethane (3×50 mL). The organic phases were combined and the solvent was removed under reduced pressure. The resulting crude product was purified with Biotage flash chromatography (MeOH/CH$_2$Cl$_2$=40: 1~15:1). The solution was concentrated and dried in vacuo to give a clear gel (~65% yield). HPLC (C-18, 0.1% TFA/milliQ, 0.1-10% acetonitrile) showed purity of 91.08%. $^1$H NMR (CDCl$_3$) confirmed desired product and purity. LC-MS further confirmed the desired product, Timolol Conjugate B, calculated molecular weight of 550.3 and observed molecular weight of 550.

Example 9

Preparation of Timolol Conjugate C

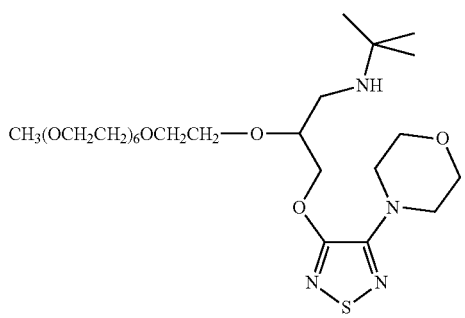

"Timolol Conjugate C"

Timolol (0.4 mmol, 140.0 mg), was dissolved in 5 ml anhydrous THF. Sodium hydride (60% dispersion in mineral oil) (0.8 mmol, 52.8 mg) was added to the timolol solution and the solution was stirred at room temperature for ten minutes. mPEG$_7$-Br (1.4 equivalents) was dissolved in 0.50 ml THF and the solution was added to reaction mixture. The reaction mixture was stirred 16 hours at room temperature. The reaction mixture was washed with an excess amount of saturated ammonium chloride solution and the product was extracted in dichloromethane (3×50 mL). The organic phases were combined and the solvent was removed under reduced pressure. The resulting crude product was purified with Biotage flash chromatography (MeOH/CH$_2$Cl$_2$=40:1~15:1). The solution was concentrated and dried in vacuo to give a clear gel (~62% yield). HPLC (C-18, 0.1% TFA/milliQ, 0.1-10% acetonitrile) showed purity of 87.39%. $^1$H NMR (CDCl$_3$) confirmed desired product and purity. LC-MS further confirmed the desired product, Timolol Conjugate C, calculated molecular weight of 638.36 and observed molecular weight of 638.

Example 10

Preparation of Timolol Conjugate D

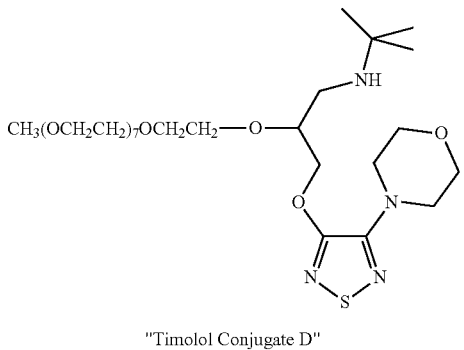

"Timolol Conjugate D"

Timolol (0.4 mmol, 140.0 mg), was dissolved in 5 ml anhydrous THF. Sodium hydride (60% dispersion in mineral oil) (0.8 mmol, 52.8 mg) was added to timolol solution and the solution was stirred at room temperature for ten minutes. mPEG$_8$-Br (1.4 equivalents) was dissolved in 0.50 ml THF and the solution was added to reaction mixture. The reaction mixture was stirred 16 hours at room temperature. The reaction mixture was washed with an excess amount of saturated ammonium chloride solution and the product was extracted in dichloromethane (53×50 mL). The organic phases were combined and the solvent was removed under reduced pressure. The resulting crude product was purified with Biotage flash chromatography (MeOH/CH$_2$Cl$_2$=40:1~15:1). The solution was concentrated and dried in vacuo to give a clear liquid (~60% yield). HPLC (C-18, 0.1% TFA/milliQ, 0.1-10% acetonitrile) showed purity of 92.66%. $^1$H NMR (CDCl$_3$) confirmed desired product and purity. LC-MS further confirmed the desired product, Timolol Conjugate D, calculated molecular weight of 682.38 and observed molecular weight of 682.

Example 11

Binding Assay—Beta-2 Adrenergic Receptors

In an adrenergic, beta-2 (human) binding assay, the following IC$_{50}$ values were obtained, as shown in Table 1.

Briefly, human promyelocytic leukemia cells (HL-60 cells) were washed and physiological buffer was added before analysis. To this was added 300 μM IBMX to inhibit phosphodiesterase. The compound of interest or antagonist control (propranolol) was added; added also was 100 nM (final) isoproterenol for 20 minutes at room temperature. Cells were then centrifuged, buffer removed and 0.1 M HCL was added to stop the reaction. EIA was performed and alkaline phosphatase activity was read at 405 nm. See Seifert et al. (1992) Eur. J. Biochem. 203 (1-2): 143-51.

TABLE 1

Various IC$_{50}$ values of compounds prepared in examples 1-6

| Drug | IC$_{50}$ (M) |
| --- | --- |
| Alprenolol | $1.23 \times 10^{-9}$ |
| Propranolol | $1.43 \times 10^{-9}$ |
| Propranolol Compound F* | $1.66 \times 10^{-6}$ |
| Propranolol Compound E* | $1.68 \times 10^{-6}$ |
| Propranolol Compound B* | $13.2 \times 10^{-6}$ |
| Propranolol Compound A | $1.12 \times 10^{-7}$ |
| Propranolol Compound D | $3.78 \times 10^{-7}$ |
| Propranolol Compound C | $3.39 \times 10^{-7}$ |

*Propranolol = 4.3 nM (IC$_{50}$)

Example 12

Binding Assay—Beta-1 Adrenergic Receptors

In an adrenergic, beta-1 (human) binding assay, the following IC$_{50}$ values were obtained, as shown in Table 2. Briefly, Human recombinant Sf9 cells were used, wherein reactions were carried out in 50 mM HEPES [pH 7.4] containing 3 mM MgCl$_2$, 0.1 μM GDP, 10 μm/mL Saoonin, and 1 mM DTT (dithiothreitol). The compound of interest was added to the membrane and then incubated for ten minutes at room temperature. Then, 30 nM of isoproterenol [final] to each well was added and allowed to incubate for an additional 30 minutes. Europium fluorescence was measured in a time-resolved fluorometer in order to ascertain any functional antagonist activity at the adrenergic beta-1 site. See Frang et al. (2003) Assay and Drug Development Technology, 1 and Minneman et al. (1979) Mol. Pharmacol. 16:34-46.

TABLE 2

IC$_{50}$ values of compounds prepared in examples 1-6

| Drug | IC$_{50}$ (M) |
| --- | --- |
| Alprenolol | $2.83 \times 10^{-8}$ |
| Propranolol | $2.05 \times 10^{-8}$ |
| Propranolol Conjugate F* | $5.39 \times 10^{-6}$ |
| Propranolol Conjugate E* | $124 \times 10^{-6}$ |
| Propranolol Conjugate B* | $3.81 \times 10^{-6}$ |
| Propranolol Conjugate A | $1.79 \times 10^{-6}$ |
| Propranolol Conjugate D | $3.78 \times 10^{-7}$ |
| Propranolol Conjugate C | $4.96 \times 10^{-6}$ |

Propranolol = $3.58 \times 10^{-8}$ (IC$_{50}$)

Example 13

Binding Assay—Beta-2 Adrenergic Receptors

In an adrenergic, beta-2 (human) binding assay, the following IC$_{50}$ values were obtained, as shown in Table 3.

Briefly, human promyelocytic leukemia cells (HL-60 cells) were washed and physiological buffer was added before analysis. To this was added 300 μM IBMX to inhibit phosphodiesterase. The compound of interest or antagonist control (propranolol) was added; added also was 100 nM (final) isoproterenol for 20 minutes at room temperature. Cells were then centrifuged, buffer removed and 0.1 M HCL was added to stop the reaction. EIA was performed and alkaline phosphatase activity was read at 405 nm. See Seifert et al. (1992) Eur. J. Biochem. 203 (1-2): 143-51.

TABLE 3

Various IC$_{50}$ Values of Compounds Prepared in Examples 7-10

| Drug | IC$_{50}$ (M) |
|---|---|
| Alprenolol | 2.40 × 10$^{-9}$ |
| Timolol Compound A | 4.59 × 10$^{-6}$ |
| Timolol Compound C* | 6.03 × 10$^{-7}$ |
| Timolol Compound B | 1.29 × 10$^{-6}$ |
| Timolol Compound D* | 6.29 × 10$^{-7}$ |

*Alprenolol = 3.46 nM (IC$_{50}$)

Example 14

Binding Assay—Beta-1 Adrenergic Receptors

In an adrenergic, beta-1 (human) binding assay, the following IC$_{50}$ values were obtained, as shown in Table 4. Briefly, Human recombinant Sf9 cells were used, wherein reactions were carried out in 50 mM HEPES [pH 7.4] containing 3 mM MgCl$_2$, 0.1 µM GDP, 10 µm/mL Saoonin, and 1 mM DTT (dithiothreitol). The compound of interest was added to the membrane and then incubated for ten minutes at room temperature. Then, 30 nM of isoproterenol [final] to each well was added and allowed to incubate for an additional 30 minutes. Europium fluorescence was measured in a time-resolved fluorometer in order to ascertain any functional antagonist activity at the adrenergic beta-1 site. See Frang et al. (2003) Assay and Drug Development Technology, 1 and Minneman et al. (1979) Mol. Pharmacol. 16:34-46.

TABLE 4

IC$_{50}$ values of compounds prepared in examples 7-10

| Drug | IC$_{50}$ (M) |
|---|---|
| Alprenolol | 1.29 × 10$^{-8}$ |
| Timolol Compound A | N/A |
| Timolol Compound C | 2.00 × 10$^{-6}$ |
| Timolol Compound B | 5.17 × 10$^{-6}$ |
| Timolol Compound D | 2.73 × 10$^{-6}$ |

What is claimed is:

1. A method of treating hypertension, cardiac arrhythmia, migraines, congestive heart failure, angina, anxiety, or depression, comprising:
administering an effective amount of a compound of the following formula to a patient in need thereof:

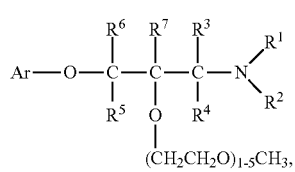

(Formula I-C)

wherein:
R$^1$ is lower alkyl;
R$^2$ is hydrogen;
R$^3$ is H;
R$^4$ is H;
R$^5$ is H;
R$^6$ is H;
R$^7$ is H;
Ar is

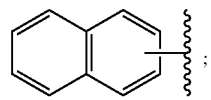

and
where

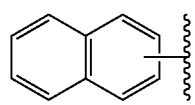

optionally bears one or more halo, alkyl, alkoxy, or acyl substituents.

2. The method of claim 1, wherein the compound is according to Formula II:

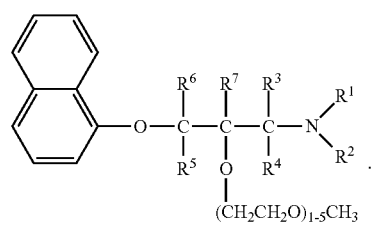

(Formula II)

3. The method of claim 1, wherein the compound is selected from

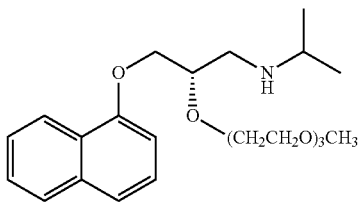

and

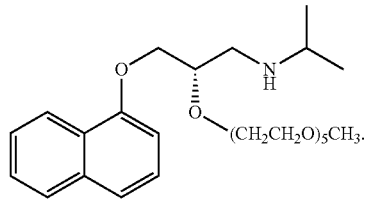

4. The method of claim 1, wherein said administering comprises orally administering the compound.

5. The method of claim 1, wherein the compound is provided in a composition comprising a pharmaceutically acceptable excipient.

6. The method of claim 1, wherein the compound is present in a dosage form.

7. The method of claim 6, wherein the dosage form is selected from a tablet, a caplet, a capsule, a gel cap, a suspension, a solution, an elixir, and a syrup.

8. The method of claim 1, wherein the effective amount is 0.01 mg/day to 750 mg/day.

9. The method of claim 1, wherein the effective amount is 0.10 mg/day to 500 mg/day.

10. The method of claim 1, wherein said administering comprises administering on a dosing schedule selected from five times a day, four times a day, three times a day, twice daily, and once daily.

* * * * *